United States Patent
Ware et al.

(10) Patent No.: US 6,668,193 B2
(45) Date of Patent: Dec. 23, 2003

(54) METHOD AND APPARATUS FOR CARDIAC SHOCK THERAPY

(75) Inventors: Kurt Ware, Vadnais Heights, MN (US); Robert S. Harguth, Ham Lake, MN (US); Kristine M. Larsen-Kelly, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 223 days.

(21) Appl. No.: 09/754,099

(22) Filed: Jan. 4, 2001

(65) Prior Publication Data

US 2002/0087196 A1 Jul. 4, 2002

(51) Int. Cl.$^7$ ................................. A61N 1/38
(52) U.S. Cl. ................. 607/5; 607/8; 607/14; 607/16
(58) Field of Search ............... 607/4, 5, 7, 8, 607/14, 16

(56) References Cited

U.S. PATENT DOCUMENTS

| | | | | |
|---|---|---|---|---|
| 4,998,531 | A | 3/1991 | Bocchi et al. | 128/419 D |
| 5,749,904 | A | 5/1998 | Gliner et al. | 607/7 |
| 5,749,905 | A | 5/1998 | Gliner et al. | 607/7 |
| 5,769,872 | A | 6/1998 | Lopin et al. | 607/5 |
| 5,776,166 | A | 7/1998 | Gliner et al. | 607/7 |
| 5,782,880 | A | 7/1998 | Lahtinen et al. | 607/9 |
| 5,792,189 | A | 8/1998 | Gray et al. | 607/5 |
| 5,797,967 | A | 8/1998 | KenKnight | 607/4 |
| 5,797,968 | A | 8/1998 | Lopin et al. | 607/5 |
| 5,800,462 | A | 9/1998 | Lopin et al. | 607/7 |
| 5,800,463 | A | 9/1998 | Lopin et al. | 607/8 |
| 5,803,927 | A | 9/1998 | Cameron et al. | 607/5 |
| 5,827,326 | A | 10/1998 | Kroll et al. | 607/5 |
| 5,833,712 | A | 11/1998 | Krull et al. | 607/7 |
| 5,836,978 | A | 11/1998 | Gliner et al. | 607/7 |
| 5,893,881 | A * | 4/1999 | Elsberry et al. | 607/5 |
| 5,904,706 | A | 5/1999 | Ayati et al. | 607/5 |
| 5,908,443 | A | 6/1999 | Brewer et al. | 607/8 |
| 5,913,877 | A | 6/1999 | Kroll et al. | 607/5 |
| 5,957,956 | A | 9/1999 | Kroll et al. | 607/5 |
| 5,968,080 | A | 10/1999 | Brewer et al. | 607/8 |
| 5,978,706 | A | 11/1999 | Brewer et al. | 607/8 |
| 6,253,108 | B1 * | 6/2001 | Rosborough et al. | 607/14 |
| 6,259,949 | B1 * | 7/2001 | Rosborough et al. | 607/14 |
| 6,263,241 | B1 * | 7/2001 | Rosborough et al. | 607/6 |
| 6,298,267 | B1 * | 10/2001 | Rosborough et al. | 607/6 |

* cited by examiner

*Primary Examiner*—Hieu T Vo
*Assistant Examiner*—Johnny H. Hoang
(74) *Attorney, Agent, or Firm*—Schwegman, Lundberg, Woessner & Kluth, P.A.

(57) ABSTRACT

An apparatus and method for delivering defibrillation shock therapy employing a multi-terminal pulse output circuit. In such a circuit, at least three electrode lead terminals are switchably connected to the positive and negative terminals of an energy storage capacitor. By serially switching selected electrode lead terminals to the capacitor terminals, a variety of shock pulse waveforms may be generated.

12 Claims, 2 Drawing Sheets

METHOD AND APPARATUS FOR CARDIAC SHOCK THERAPY

FIELD OF THE INVENTION

This invention pertains to apparatus and methods for treating cardiac arrhythmias. In particular, the invention relates to an apparatus and method for electrically terminating tachyarrhythmias.

BACKGROUND

Tachyarrhythmias are abnormal heart rhythms characterized by a rapid heart rate. Examples of tachyarrhythmias include supraventricular tachycardias such as sinus tachycardia, atrial tachycardia, and atrial fibrillation (AF), and ventricular tachyarrhythmias such as ventricular tachycardia (VT) and ventricular fibrillation (VF). Both ventricular tachycardia and ventricular fibrillation are hemodynamically compromising, and both can be life-threatening. Ventricular fibrillation, however, causes circulatory arrest within seconds and is the most common cause of sudden cardiac death. Atrial fibrillation is not immediately life threatening, but since atrial contraction is lost, the ventricles are not filled to capacity before systole which reduces cardiac output. This may cause lightheadedness or fainting in some individuals, as well as fatigue and shortness of breath, hindering the individual from carrying out normal daily activities. If atrial fibrillation remains untreated for long periods of time, it can also cause blood to clot in the left atrium, possibly forming emboli and placing patients at risk for stroke.

Cardioversion (an electrical shock delivered to the heart synchronously with an intrinsic depolarization) and defibrillation (an electrical shock delivered without such synchronization) can be used to terminate most tachyarrhythmias, including AF, VT, and VF. As used herein, the term defibrillation should be taken to mean an electrical shock delivered either synchronously or not in order to terminate a fibrillation. In electrical defibrillation, a current depolarizes a critical mass of myocardial cells so that the remaining myocardial cells are not sufficient to sustain the fibrillation. The electric shock may thus terminate the tachyarrhythmia by depolarizing excitable myocardium, which thereby prolongs refractoriness, interrupts reentrant circuits, and discharges excitatory foci.

Implantable cardioverter/defibrillators (ICDs) provide electrotherapy by delivering a shock pulse to the heart when fibrillation is detected by the device. The ICD is a computerized device containing a pulse generator that is usually implanted into the chest or abdominal wall. Electrodes connected by leads to the ICD are placed on the heart, or passed transvenously into the heart, to sense cardiac activity and to conduct the impulses from the pulse generator. Typically, the leads have electrically conductive coils along their length that act as electrodes. ICDs can be designed to treat either atrial or ventricular tachyarrhythmias, or both, by delivering a shock pulse that impresses an electric field between the electrodes to which the pulse generator terminals are connected. The electric field vector applied to the heart is determined by the magnitude of the voltage pulse and the physical arrangement of the shocking electrodes, which may serve to concentrate the field in a particular region of the heart. Thus, the particular electrode arrangement used will dictate how much depolarizing current is necessary in order to terminate a given tachyarrhythmia.

Ventricular and atrial fibrillation are phenomena that exhibit a threshold with respect to the shock magnitude and duration needed to terminate the fibrillation by changing the transmembrane potential in a critical mass of myocardial cells. The ventricular defibrillation threshold (VDFT), for example, is the smallest amount of energy that can be delivered to the heart to reliably convert ventricular fibrillation to normal sinus rhythm. Similarly, the atrial defibrillation threshold (ADFT) is the threshold amount of energy that will terminate an atrial fibrillation. The larger the magnitude of the shocks delivered by an ICD, the more the battery is drained, thus decreasing the longevity of the device. It is desirable, therefore, for the defibrillation threshold to be as small as possible in order to minimize the amount of shocking current that the ICD must deliver in order to terminate a given tachyarrhythmia.

Electrode arrangements have been devised in an attempt to minimize the defibrillation threshold for particular types of tachyarrhythmias. For example, the traditional configuration for ventricular defibrillation is to place a cathodic electrode in the right ventricle, with the anode formed jointly by an electrode placed in the superior vena cava and the conductive housing of the ICD acting as an additional electrode. For treating atrial fibrillation, a conventional electrode configuration is to use electrodes disposed within the coronary sinus and in the right atrium. In addition, the waveform of the shocking pulse also affects the defibrillation threshold. ICDs use a capacitor discharge system for delivering shock pulses in which a charged capacitor is connected to the shock electrodes to deliver current to the myocardium. Because of space constraints, the size of a typical capacitor is limited and thus exhibits a significant exponential decay when connected to the load (i.e., a small RC time constant). Rather than allowing the decay to continue when the capacitor is connected across the load, solid-state switches may be used to sharply truncate the waveform which may result in a lower energy requirement for defibrillation. ICDs also commonly employ a biphasic shock pulse waveform in which the polarity of the waveform reverses during the shock pulse, a technique that has been found to further lower the defibrillation threshold. (See U.S. Pat. No. 4,998,531, hereby incorporated by reference.)

In order to further improve safety and avoid unnecessary discomfort for ICD patients, there is a continuing need for methods and apparatus that improve the efficiency of electrical defibrillation and thereby reduce the defibrillation threshold. Such reductions in defibrillation thresholds may also expand the population of patients for whom ICDs are an appropriate therapeutic option. It is toward this general objective that the present invention is directed.

SUMMARY OF THE INVENTION

The present invention is a method and apparatus for terminating tachyarrhythmias such as fibrillation by the efficient delivery of electrical energy through an electrode configuration to the heart. A shock pulse output circuit in accordance with the invention includes a storage capacitor with positive and negative terminals and further includes at least three electrode lead terminals with each such electrode lead terminal switchably connected to the positive and negative capacitor terminals. Control circuitry then switches selected electrode lead terminals to either the positive or negative capacitor terminal in order to impose the capacitor voltage between electrode lead terminals and deliver a shock pulse. By serially switching selected electrode lead terminals to selected capacitor terminals, the control circuitry may thus generate a defined shock pulse waveform. For example, selected electrode lead terminals can be switched between different capacitor terminals in a manner that reverses the polarity of the voltage between the terminals to deliver a biphasic or multiphasic shock pulse. The particular electrodes used to deliver a conventional shock pulse are determined by the programming of the control circuitry, allowing for easy modification. The multi-terminal pulse output circuit also allows for more complex shock pulse waveforms to be generated by using different electrode lead terminals during the same pulse output cycle.

DESCRIPTION OF PARTICULAR EMBODIMENTS

Figure 1:
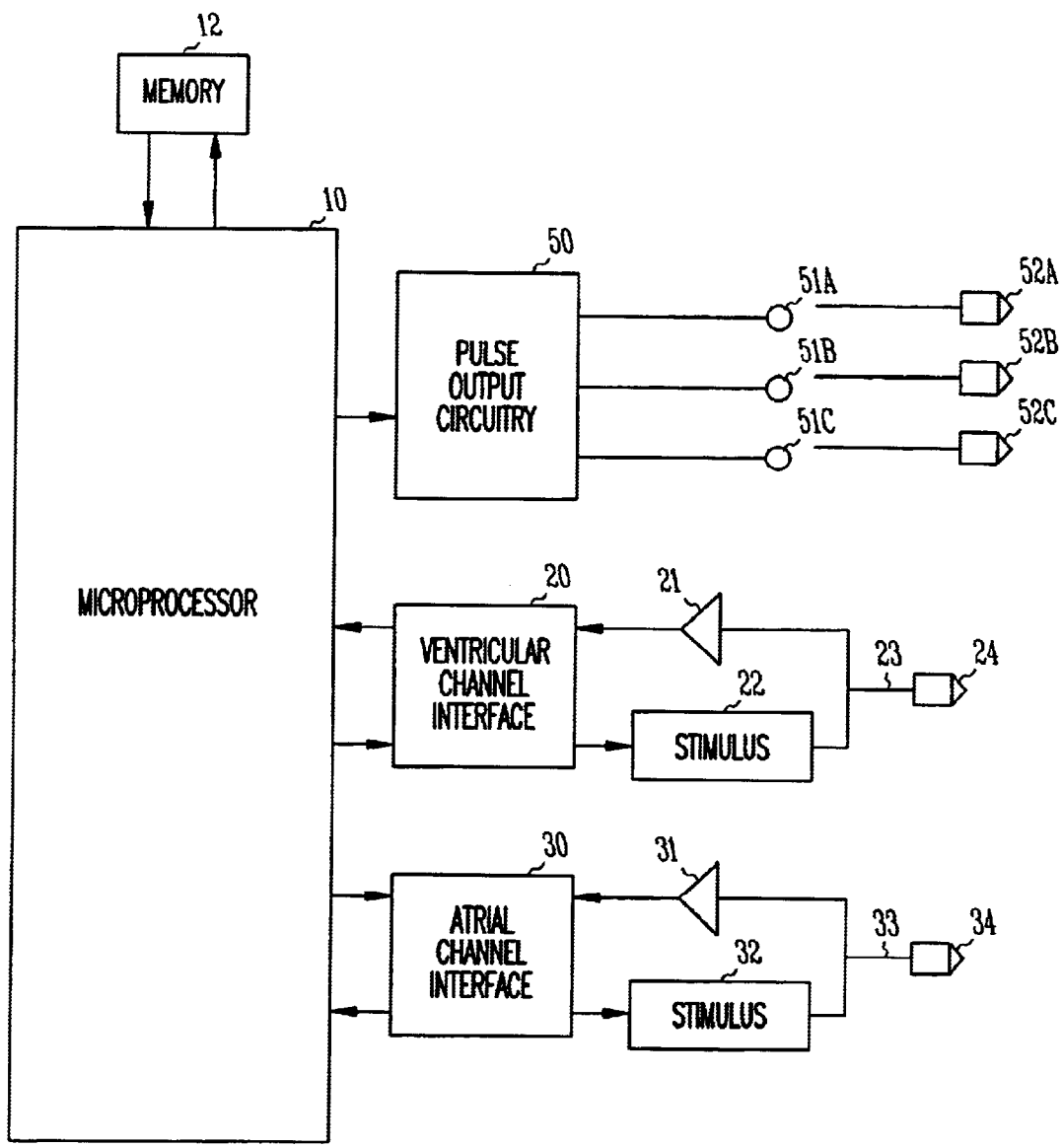
FIG. 1 is a system diagram of an apparatus for terminating tachyarrhythmias with electrical energy.

FIG. 1 is a system diagram of a microprocessor-based implantable cardioverter/defibrillator with the capability of also delivering pacing therapy. A microprocessor 10 communicates with a memory 12 via a bidirectional bus. The memory 12 typically comprises a ROM or RAM for program storage and a RAM for data storage. The ICD has atrial sensing and pacing channels comprising electrode 34, lead 33, sensing amplifier 31, pulse generator 32, and an atrial channel interface 30 which communicates bidirectionally with a port of microprocessor 10. The ventricular sensing and pacing channels similarly comprise electrode 24, lead 23, sensing amplifier 21, pulse generator 22, and a ventricular channel interface 20 which communicates bidirectionally with a port of microprocessor 10. For each channel, the same lead and electrode are used for both sensing and pacing. The sensing channels are used to control pacing and for measuring heart rate in order to detect tachyarrhythmias such as fibrillation. The ICD detects a ventricular tachyarrhythmia, for example, by measuring a heart rate via the ventricular sensing channel and determining whether the rate exceeds a selected threshold value. A telemetry interface is also typically provided enabling the programming of the microprocessor to be modified using an external programmer.

A pulse output circuit 50 is also interfaced to the microprocessor for delivering cardioversion or defibrillation pulses to the heart via electrode lead terminals 51a through 51c that are connected by electrode leads to shock electrodes 52a through 52c placed in proximity to regions of the heart. The electrode leads have along their length electrically conductive coils that act as electrodes for defibrillation stimuli. The electrode leads and electrodes used in any of the described embodiments below may be implemented as lead-body electrodes that are either single elongated coils or made up of a plurality of smaller bands. The pulse output circuitry as well as the rest of the device are powered by a battery power supply. The device is enclosed by a case which may be implanted by placing it an abdominal wall pocket, or preferably, in a pectoral pocket either subcutaneously or under the pectoralis major muscle. The leads from the housing are typically advanced to the heart transvenously, with venous access through the cephalic or subclavian veins.

Figure 2:
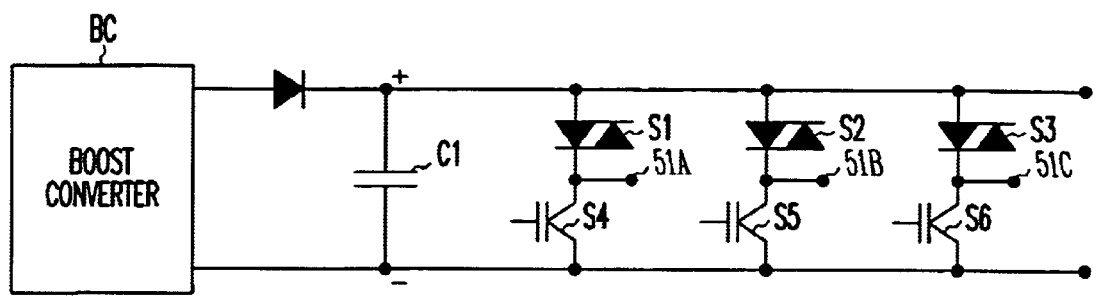
FIG. 2 shows the pulse output circuitry in an exemplary embodiment of the invention.

FIG. 2 shows a pulse output circuit in accordance with the present invention. An energy storage capacitor C1 is used to store an electrical charge which is delivered to the heart in the form of a selected pulse waveform. The capacitor C1 may be a single capacitor or may be made up of multiple capacitors connected in series or parallel. In any case, the capacitor C1 is charged to a high voltage from a low voltage battery by a boost converter BC that is basically a step-up switching voltage regulator. The shock electrodes are connected to electrode lead terminals 51a through 51c which are switchably connected to the energy storage capacitor C1 by switches S1 through S6. When a shock pulse is delivered, selected electrode lead terminals are connected by the aforementioned switches to the positive or negative terminals of the capacitor C1 to thereby impress the capacitor voltage across the shock electrodes to which the selected terminals are connected. Switches S1, S2, and S3 are remote gate thyristors or silicon controlled rectifiers having gate voltages that are controlled by the microprocessor 10. Switches S4 through S6 are insulated gate bipolar transistors also having microprocessor-controlled gate voltages. By controlling the state of the switches, the microprocessor can control the polarity of the shock pulse delivered to selected electrodes to deliver monophasic, biphasic, or multiphasic shock waveforms. As will be described below, the microprocessor may also select different electrodes during the pulse output cycle.

The pulse output circuit described above permits a great deal of flexibility with respect to the type of shock pulse waveform that may be delivered. For example, a selected pair of electrode lead terminals may simply be switched to different terminals of the energy storage capacitor and then switched off to deliver a monophasic shock pulse. By switching the lead terminals to opposite capacitor terminals midway through the pulse cycle in order to reverse the polarity of the waveform, a biphasic pulse may be delivered. Similarly, the polarity of the waveform can be reversed multiple times to deliver a multiphasic pulse. These types of shock waveforms can be generated by a two-terminal H-bridge type of output circuit. As will be described below, however, a multi-terminal output circuit provides additional pulse output configurations such as using different pairs of electrodes to deliver successive shock pulses, connecting certain electrodes in common during the pulse, and generating more complex waveforms using multiple electrodes that can vary spatially as well as temporally during the pulse cycle.

In one embodiment, a pulse output configuration can be implemented which is particularly suited for terminating atrial arrhythmias. In this configuration, an electrode lead is connected to a first shocking electrode which is situated in the coronary sinus such that the electrode resides in the left lateral heart. The electrode lead terminal is then switched to a capacitor terminal so as to act as a cathode during a monophasic voltage pulse. A second shocking electrode is disposed within the superior vena cava and is switched through its lead to the other capacitor terminal so as to form an anode during the voltage pulse. The case of the device may be switched to a capacitor terminal so as to form a third electrode in common with one of the others. For example, the coronary sinus electrode may act as the sole cathode while the superior vena cava and case electrodes act as joint anodes for a monophasic defibrillation stimulus. In other embodiments, the polarity of the waveform can be reversed or can be reversed mid-cycle to generate a biphasic waveform. In another embodiment, a pulse output configuration that is particularly suited for ventricular defibrillation is employed. A lead with a first distal shocking electrode is situated in the right ventricle, with its electrode lead switched to one terminal of the capacitor so as to act as a cathode during a monophasic voltage pulse. Second and third shocking electrodes are switched through their respective leads to the other terminal of the capacitor so as to form a joint anode during the voltage pulse and are disposed within the superior vena cava and coronary sinus, respectively. The conductive case of the device may be switched to a capacitor terminal in common with the second and third electrodes so as to also constitute the joint anode. Many other pulse output configurations using arrangements of multiple shocking electrodes are, of course, possible. For example, a four electrode arrangement may be used which includes the device case as one electrode and shocking electrodes disposed in the superior vena cava, the coronary sinus, and the right ventricle.

Although a conventional two-terminal pulse output circuit may have multiple electrodes hardwired to its capacitor terminals in order to implement either of the just described pulse output configurations, a multi-terminal pulse output circuit in accordance with the present invention may be programmed to implement any pulse output configuration that its physical arrangement of electrodes is capable of supporting. Using an external programmer, the pulse output algorithms executed by the microprocessor may be modified so as to use any of the connected electrodes as cathodes or anodes during a pulse output. Thus, a clinician may select a particular pulse output configuration initially and change to another one after an evaluation period by simply reprogramming the device.

The pulse output configurations described so far have been ones in which selected shock electrodes are grouped together throughout the pulse output cycle while being switched to one or both capacitor terminals. A pulse output circuit in accordance with the present invention, however, may be programmed to serially switch any of the physically connected shock electrodes to either of the capacitor terminals at selected times during the pulse output cycle. Complex pulse output waveforms, in which different electrodes are used as cathodes and anodes during the pulse output cycle, may thus be delivered.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. An apparatus for delivering defibrillation shock pulses, comprising:
   a sensing channel for detecting electrical events in the heart and producing sensing signals in accordance therewith;
   processing circuitry for detecting the occurrence of a tachyarrhythmia from the sensing signals;
   pulse output circuitry for delivering shock pulses, the circuitry including a storage capacitor with positive and negative terminals and further including at least three electrode lead terminals with each such electrode lead terminal switchably connected to the positive and negative capacitor terminals;
   control circuitry for switching a selected electrode lead terminal to either the positive or negative capacitor terminal to impose a capacitor voltage between electrode lead terminals and deliver a shock pulse, the control circuitry including voltage-controlled metal-oxide semiconductor switches for switching the electrode lead terminals to a capacitor terminal.

2. The apparatus of claim 1 further comprising shock electrodes for connection to electrode lead terminals and disposition in proximity to the heart.

3. The apparatus of claim 1 wherein the control circuitry is configured to serially switch selected electrode lead terminals to selected capacitor terminals in order to generate a defined shock pulse waveform.

4. The apparatus of claim 3 wherein the control circuitry is configured to serially switch a selected pair of electrode lead terminals between different capacitor terminals to reverse the polarity of the voltage between the terminals and thereby deliver a biphasic shock pulse.

5. The apparatus of claim 3 wherein the control circuitry is configured to serially switch successive selected pairs of electrode lead terminals to selected capacitor terminals and thereby deliver a multiphasic shock pulse.

6. The apparatus of claim 2 wherein the shock electrodes include a first electrode adapted for disposition within the coronary sinus, a second electrode adapted for disposition within the superior vena cava or right atrium, and a third electrode.

7. The apparatus of claim 6 wherein the third electrode is adapted for disposition in the right ventricle.

8. The apparatus of claim 6 wherein the third electrode is an implantable housing.

9. A shock pulse output circuit for use in an implantable defibrillator, comprising:
   a storage capacitor with positive and negative terminals;
   at least three electrode lead terminals with each such electrode lead terminal switchably connected to the positive and negative capacitor terminals; and,
   voltage-controlled switches connecting each electrode lead terminal to the positive and negative capacitor terminals such that switching of electrode lead terminals to different capacitor terminals imposes a capacitor voltage between the electrode lead terminals and delivers a shock pulse, wherein the voltage-controlled switches for switching the electrode lead terminals to a capacitor terminal are semiconductor switches.

10. A method for delivering a defibrillation shock pulse, comprising:
   providing a storage capacitor with positive and negative and at least three electrode lead terminals with each such electrode lead terminal switchably connected to the positive and negative capacitor terminals;
   serially switching selected electrode lead terminals to either the positive or negative capacitor terminal in order to impose a capacitor voltage between electrode lead terminals and deliver a shock pulse which varies spatially as well as temporally.

11. The method of claim 10 further comprising serially switching a selected pair of electrode lead terminals between different capacitor terminals to reverse the polarity of the voltage between the terminals and thereby deliver a biphasic shock pulse.

12. The method of claim 10 further comprising serially switching successive selected pairs of electrode lead terminals to selected capacitor terminals and thereby deliver a multiphasic shock pulse.

* * * * *